United States Patent [19]

Gemind

[11] 4,088,126
[45] May 9, 1978

[54] DEVICE FOR MEASURING BLOOD PRESSURE

[76] Inventor: John M. Gemind, Copley, Ohio

[21] Appl. No.: 689,074

[22] Filed: May 24, 1976

[51] Int. Cl.² .............................................. A61B 5/02
[52] U.S. Cl. .......................... 128/2.05 G; 128/2.05 M
[58] Field of Search .................... 128/2.05 G, 2.05 M, 128/2.05 A, 2.05 C, 2.05 R

[56] References Cited

U.S. PATENT DOCUMENTS

| | | | |
|---|---|---|---|
| 2,624,334 | 1/1953 | Epstein | 128/2.05 G |
| 2,952,253 | 9/1960 | Seligman et al. | 128/2.05 G |
| 3,252,459 | 5/1966 | Hay | 128/2.05 G |
| 3,349,763 | 10/1967 | Clements, Jr. et al. | 128/2.05 M |
| 3,543,745 | 12/1970 | Rosenstein | 128/2.05 G |
| 3,905,353 | 9/1975 | Lichowsky | 128/2.05 G |

*Primary Examiner*—Kyle L. Howell
*Attorney, Agent, or Firm*—Michael L. Gill

[57] ABSTRACT

A device for use in measuring blood pressure including an inflatable cuff, a hand inflating bulb and a vibrating diaphragm pump powered by a special coil and utilizing rectified electrical power.

5 Claims, 4 Drawing Figures

DEVICE FOR MEASURING BLOOD PRESSURE

The foregoing abstract is not to be taken as limiting the invention of this application, and in order to understand the full nature and extent of the technical disclosure of this application, reference must be made to the accompanying drawing and the following detailed description.

BACKGROUND OF THE INVENTION

This invention relates to blood pressure measuring devices and particularly to an inexpensive portable device which will relieve the strain encountered when continuously taking blood pressures.

In the most common method of taking blood pressure, an inflatable cuff or armlet is wrapped around the patient's arm and is inflated by means of a hand bulb to a pressure somewhat above the systolic pressure. By manipulating a bleed-off valve located between the cuff and bulb (usually adjacent the bulb) the pressure is slowly reduced through the systolic pressure which is determined with the aid of a stethoscope. The pressure is then reduced rather quickly until it approaches the diastolic range at which time the rate of pressure drop is reduced and the diastolic pressure determined with the aid of the stethoscope.

This method of taking blood pressure is quite adequate in many instances. However, when one person is repeatedly taking blood pressures such as at an American Red Cross Bloodmobile or a blood pressure station, his hand will quickly become tired from squeezing the inflation bulb.

Attempts in the past at providing relief for the nurse or technician repeatedly taking blood pressures have only met with limited success since, to the knowledge of the inventor, no convenient, portable device is available.

SUMMARY OF THE INVENTION

The present invention provides a simple, reliable system for use in measuring blood pressure which is compact and inexpensive. A vibrating pump powered by a special coil is adapted to be connected to the hand bulb of a cuff or armlet. A foot-operated switch activates the pump which quickly and safely inflates the cuff.

An apparatus is provided in conjunction with an inflatable cuff of the type having a single passage for inflating and deflating the cuff, and a hand bulb with a check valve for inflating the cuff and blocking off blood flow in a patient's arm. The apparatus comprises a vibrating pump including means to restrict air flow to one direction at all times. A flexible conduit extends from the outlet of the pump and a means interchangeable with the check valve is connected to the end of the conduit remote from the pump so that the pump can inflate the cuff through the bulb.

It is an object, therefore, of the present invention to provide a simple portable device for use in measuring blood pressure.

Other objects and advantages will be in part apparent and in part pointed out more in detail hereinafter.

The invention accordingly consists in the features of construction, combination of elements, and arrangement of parts, which will be exemplified in the construction hereinafter set forth and the scope of the application of which will be indicated in the appended claims.

DETAILED DESCRIPTION OF THE INVENTION

Figures 1, 2, 3, 4:
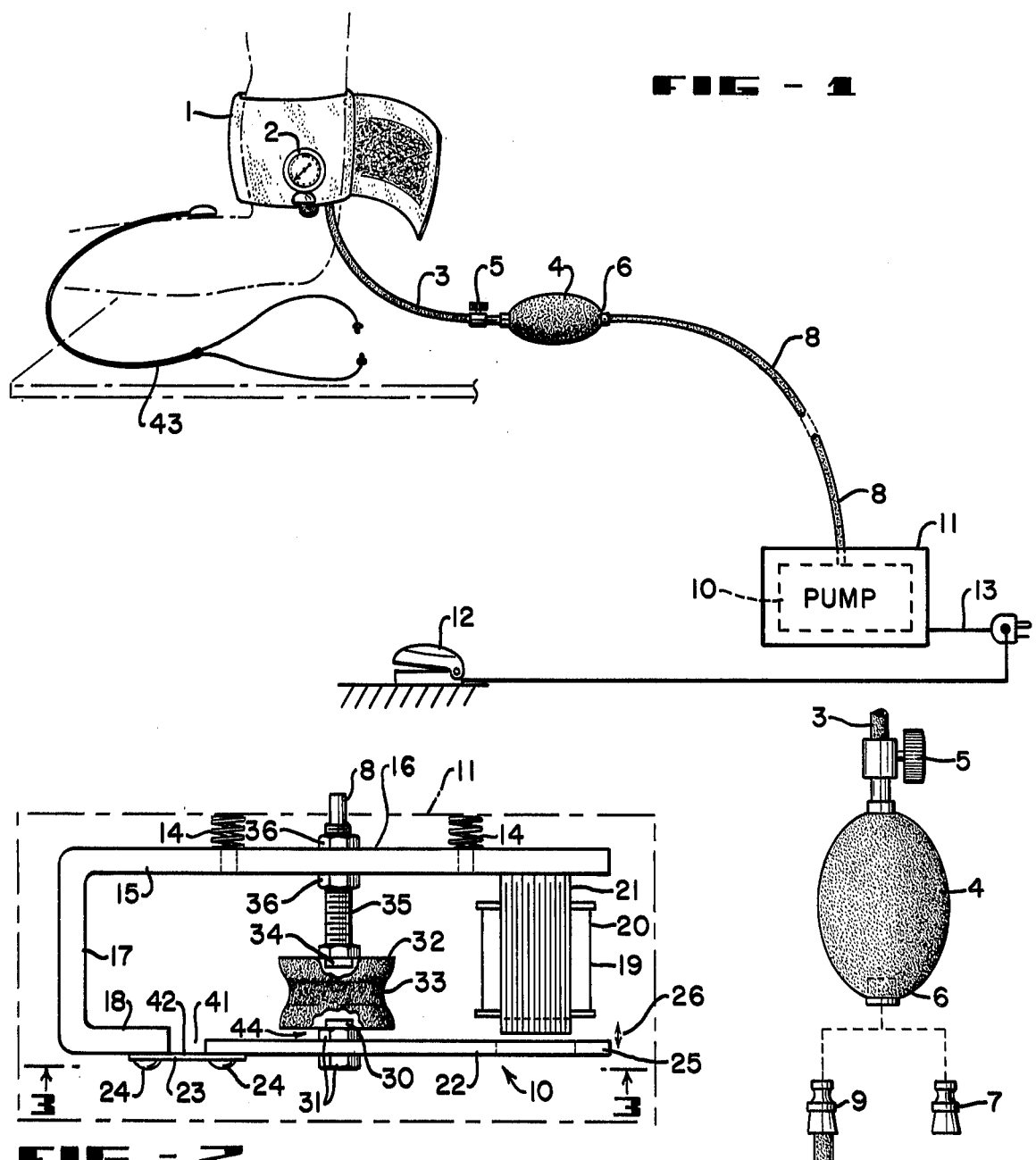
FIG. 1 is a schematic view of the device of the present invention.
FIG. 2 is an elevational view of a pump made in accordance with the present invention.
FIG. 3 is a view of the pump of FIG. 2 taken along line 3—3 of FIG. 2.
FIG. 4 is a view of the hand inflating ball shown in FIG. 1 but illustrating the interchangeability of the pump line with a check valve.

With reference to the drawing and in particular FIG. 1, there is illustrated a standard inflatable cuff or armlet 1, including a pressure gauge 2 for indicating the pressure in the cuff 1. A flexible tube or conduit 3 extends from the cuff 1 to a hand pressurizing bulb 4. A bleed-off valve 5 is provided in the tube 3 between the cuff 1 and the bulb 4. The valve 5 is conveniently placed acjacent the bulb 4 in order that the valve 5 can be turned with the thumb and forefinger of the hand on the bulb 4 to release the pressure in the cuff 1.

Referring now to FIG. 4, the end 6 of the bulb 4 opposite the bleed-off valve 5 is normally adapted to receive a check valve 7. In accordance with the present invention, a second flexible tube or conduit 8 is provided with a fitting 9 that is adapted to be received in the end 6 of the bulb 4 in place of the check valve 7. The valve 7 and fitting 9 are thus quickly interchangeable so the cuff 1 can be used with or without the pump as the need arises.

Returning now to FIG. 1, the second tube 8 extends between the bulb 4 and a pump 10 which is packaged in a sound-dampening box 11. A foot-operated switch 12 is connected to the power supply line 13 to activate and deactivate the pump 10.

With reference to FIGS. 2 and 3, the pump 10 is suspended from the top of the box 11 (shown only in dashed lines in FIG. 2) by means of a pair of coil springs 14. The pump 10 comprises a flat steel frame 15 bent in the general shape of the letter J with the long or major side 16 of the J extending horizontally and the hooked part 17 extending downwardly. The short end 18 of the hooked part 17 extends horizontally in parallel relationship with the major side 16. The springs 14 are secured to the major side 16.

An electromagnet 19, comprising a coil 20 and a laminated steel core 21, is rigidly fixed to the bottom surface of the major side 16 near the end of the frame 15 opposite or away from the hooked part 17. The coil is so arranged that it will provide vertically directed magnetic forces.

A vibrator bar 22 made of a flat steel plate is disposed beneath and parallel to the major side 16 of the frame 15 with one end 25 extending to adjacent the bottom side of the electromagnet 19. The vibrator bar 22 appears as an extension of the short end 18 and is fixed thereto by means of a spring steel plate 23. A gap 41 is provided between the vibrator bar 22 and the short end 18 to provide a flexing portion 42 in the spring steel plate 23 and permit vibration of the vibrator bar 22. In the particular embodiment illustrated, the short end 18 and the vibrator bar 22 are fixed to the spring steel plate 23 by means of rivets 24. The end 25 of the vibrator bar 22 opposite or away from the spring steel plate 23 is free and the bar 22 is free to vibrate as indicated by the two-headed arrow 26.

The end of the core 21 opposite the major side 16 has a plurality of legs 27 having spaces 28 therebetween. The end 25 of the vibrating bar 22 is provided with slots 29 which are sized and aligned with the legs 27 so that during vibration of the bar 22, the legs will repeatedly extend into the slots 29.

A one-way check valve 30 is fixed to the top side of the vibrator bar 22 by means of nuts 31 and is adapted to receive a diaphragm 32 made of suitable elastomeric material such as rubber. The diaphragm is circular and has an annular necked down portion 33 to enhance flexing and reduce fatigue failures. A second check valve 34 is received in the end of the diaphragm 32 opposite the first check valve 30 and has its outlet in communication with an externally threaded tube 35. Both check valves 30 and 34 are so arranged that air will flow into the bottom of the diaphragm 32 as indicated by the arrows 44 and out the top into the tube 8. The threaded tube 35 extends through and is fixed to the major side 16 of the frame 15 by means of nuts 36. The second tube 8 is connected to the outlet end of the threaded tube 35 completing the passage from the pump 10 to the cuff 1.

In the particular embodiment illustrated, the coil 20 has 1500 turns of wire having a total resistance of 50 ohms. There are three poles 37, 38 and 39 anchored to the coil frame with the middle pole 38 being a dummy pole. A 115, 60 cycle AC electrical source is connected to the two poles 37 and 38. A rectifier 40, which in the present embodiment is a solid state diode, is connected between the dummy pole 38 and the pole 39 to complete the circuit. In the particular embodiment illustrated, the diode is a 1.5 ampere, 600 volt PIV diode. The coil 20 therefore is powered by rectified 115 volt electricity. While the coil of the specific embodiment illustrated has 1500 turns of wire having a total resistance of 50 ohms, a coil can be used having from 1350 to 1650 turns of wire having a resistance of from 45 to 55 ohms.

The overall length of the frame 15 is 5.25 inches and the pump is drawn to scale in FIGS. 2 and 3. This small compact pump, however, is capable of safely inflating the cuff 1 to a pressure of 250 millimeters of mercury in less than five seconds. Further, if electrical power is not available or is momentarily shut off, the system can be hand operated by means of the ball 4 with the check valves 30 and 34 acting as check valves for the ball 4. Also, if desired, the tube 8 and fitting 9 can be removed and replaced by the check valve 7 providing another alternative if power is not available.

In the use of the apparatus, the cuff 1 is wrapped about the patient's arm as illustrated in FIG. 1 and is inflated by depressing the foot switch 12. When the systolic pressure is reached, which is determined with the aid of a stethoscope 43, the foot switch 12 is released stopping the pump. The bleed-off valve 5 is opened to drop the pressure slowly through the systolic range and then rapidly to about the diastolic range and finally slowly through the diastolic range. The respective pressures are determined with the use of the stethoscope 43 and recorded.

For purposes of clarity, the pump 10 has been described by referring to top and bottom or up and down. It will be appreciated, however, that the orientation of the pump relative to the vertical direction can be changed.

While a certain representative embodiment and details have been shown for the purpose of illustrating the invention, it will be apparent to those skilled in this art that various changes and modifications may be made therein without departing from the spirit or scope of the invention.

What is claimed is:

1. A device for use in measuring blood pressure comprising, in combination, an inflatable cuff means for stopping blood flow in a patient's arm, pressure gauge means operatively associated with said cuff for indicating the pressure in said cuff, an electrically powered vibrating pump, a single passage means extending between said pump and said cuff for inflating and deflating said cuff, a bleed-off valve means in said passage for releasing pressure in said cuff, a hand pressurizing bulb disposed in said passage means, said device being further characterized by said pump being a diaphram type pump and including a check valve means for cooperating with said bulb to inflate said cuff by hand.

2. A device as claimed in claim 1 further including a foot operated switch means operatively associated with said pump for starting and stopping said pump.

3. A device as claimed in claim 2 wherein said pump is powered by a coil for use with 60 cycle, 115 volt electricity, said coil having 1350 to 1650 turns of wire having a total resistance of 45 to 55 ohms and including a rectifier to rectify the alternating current.

4. A device as claimed in claim 3 wherein said coil has about 1500 turns of wire having a total resistance of about 50 ohms.

5. A device as claimed in claim 1 wherein said pump is powered by a coil for use with 60 cycle, 115 volt electricity, said coil having 1350 to 1650 turns of wire having a total resistance of 45 to 55 ohms and including a rectifier to rectify the alternating current.

* * * * *